United States Patent [19]

Sellstedt et al.

[11] 4,110,458
[45] Aug. 29, 1978

[54] N-(PYRIDYL) OXAMIC ACID DERIVATIVES

[75] Inventors: John H. Sellstedt, Pottstown; Charles J. Guinosso, King of Prussia, both of Pa.; Albert J. Begany, Tucson, Ariz.

[73] Assignee: American Home Products Corporation, New York, N.Y.

[21] Appl. No.: 834,615

[22] Filed: Sep. 19, 1977

Related U.S. Application Data

[60] Continuation-in-part of Ser. No. 669,569, Mar. 23, 1976, Pat. No. 4,054,661, which is a division of Ser. No. 542,465, Jan. 20, 1975, Pat. No. 3,966,965, which is a continuation-in-part of Ser. No. 344,466, Mar. 23, 1973, abandoned.

[51] Int. Cl.$^2$ .................... A61K 31/34; C07D 213/57
[52] U.S. Cl. ................... 424/263; 260/294.9; 260/295.5 A
[58] Field of Search .............. 260/294.9, 295.5 A; 424/263

[56] References Cited

U.S. PATENT DOCUMENTS

| | | | |
|---|---|---|---|
| 3,980,660 | 9/1976 | Wright et al. | 260/295.5 A |
| 4,038,398 | 7/1977 | Hall et al. | 260/294.9 |

OTHER PUBLICATIONS

Petyunin et al., Journal of General Chemistry, USSR, vol. 32(1), pp. 1383–1385, 1962.
Petyunin et al., Journal of General Chemistry, USSR, vol. 34(1), pp. 26–30, (1964).
Sellstedt et al., Chem. Abstracts, vol. 83(21), item no. 172,416v, Nov. 24, 1975.

*Primary Examiner*—Alan L. Rotman
*Attorney, Agent, or Firm*—Richard K. Jackson

[57] ABSTRACT

Anti-allergic agents of N-(pyridyl)-oxamic acid derivation present the following formulae:

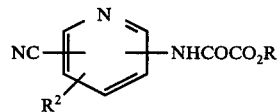

in which R is —H or lower alkyl;
  $R^2$ is —H, lower alkoxy, lower alkyl, halo or polyhalo(lower) alkyl;
or a pharmaceutically acceptable salt thereof.

17 Claims, No Drawings

N-(PYRIDYL) OXAMIC ACID DERIVATIVES

REALTED APPLICATIONS

This application is a continuation-in-part of Ser. No. 669,569, now U.S. Pat. No. 4,054,661 dated Oct. 18, 1977, Mar. 23, 1976 which is a divisional application of Ser. No. 542,465, filed Jan. 20, 1975, now U.S. Pat. No. 3,966,965, which in turn is a continuation-in-part of Ser. No. 344,466, filed Mar. 23, 1973, now abandoned.

BACKGROUND OF THE INVENTION

Atopic immediate sensitivity is the chief manifestation found in animals suffering from bronchial asthma, seasonal pollinosis (e.g. hay fever), allergic rhinitis, urticaria, allergic conjunctivities, food allergies and anaphylactoid reactions. The substances most frequently responsible for clinically manifest sensitivities are plant pollen, animal feathers and danders, dust, milk and wheat, whether inhaled or ingested. Atopic hypersensitivity is found in man, dog and other animals. Its occurrance is exceptionally found in the lower animals.

The presence of antibodies associated with atopic hypersensitivity reactions in the host serum is established by the passive sensitization of the skin of a normal recipient, after injection of serum from a sensitized host into a skin site followed by injection of antigen into the same area 24 hours later, resulting in a local hive. This is commonly referred to as the Prausnitz-Kustner (P-K) reaction.

The antibody associated with atopic hypersensitivity possesses distinctive features in that it does not in all forms precipitate with its antigen, fails to pass the placenta from mother to fetus, has special affinity for the skin, frequently lacks specificity toward an individual antigenic factor and is usually labile at about 56° C. after 2 hours.

The homocytotropic antibody found in or induced in the rat is related in function and reaction to immunoglobulin E (reagin or IgE) found in the human. The correlation between homocytotropic antibody in the rat and IgE in the human has been established through the common effects obtained from chemical reactions, immunological reactions and drug responses in the two species hosting those antibodies. In the human, reagin is the antibody responsible for atopic immediate hypersensitive reactions. In the rat, the homocytotropic antibody is responsible for atopic immediate hypersensitive reactions.

In theory, reagin, influences the cell membrane of a mast cell by reacting with an antigen, to initiate the reaction(s) within the mast cell which ultimately releases a mediator such as Bradykinin, SRS-A (slow reacting substance-A), histamine and other unknown substances. The mediator effects a change in surrounding cell wall permeability permitting a rapid change in flow or exudance of mediator(s) from the cells, resulting in an allergic attack symptom. The various methods commonly employed to relieve the symptoms of allergic attack, none of which are considered to be quite acceptable, are to (1) avoid attack by the antigen, (2) block the production of antibody with an immunosuppressant, (3) block the action of the mediators on the cell under attack by administration of anti-histaminics, anti-5-hydroxy-tryptamines(5-HT) or anti-inflammatories, or (4) stimulate the cell under attack to negate the action of the mediator through the action of bronchodilators such as Isuprel ® or a Xanthine.

A compound typifying anti-allergic activity by blocking reaction(s) within the mast cells, thereby preventing the production and release of mediators, is disodium cromoglycate. (INTAL ®).

DESCRIPTION OF THE INVENTION

In accordance with this invention, there is provided a process for preventing the release of pharmacological mediators from an immediate hypersensitivity reaction between reaginic type antibodies and an antigen, thereby preventing the symptoms manifest in bronchial asthma, seasonal pollinosis, allergic rhinitis, urticaria, allergic conjunctivitis, food allergy and anaphylactoid reactions of a sensitized animal, which comprises prophylactically administering to said animal an effective amount of a compound of the formula:

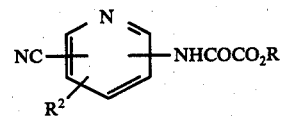

in which R is —H or lower alkyl;

$R^2$ is —H, lower alkoxy, lower alkyl, halo or polyhalo (lower, alkyl;

or a pharmaceutically acceptable salt thereof.

The N-(pyridyl) oxamic acid derivatives form an additional aspect of this invention. They present the structural formula:

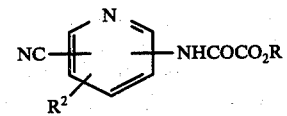

in which R is —H or lower alkyl;

$R^2$ is —H, lower alkoxy, lower alkyl, halo or polyhalo (lower) alkyl;

or a pharmaceutically acceptable salt thereof.

The term "lower" used throughout this application to modify alkyl, alkoxy, and the like, is intended to embrace univalent aliphatic hydrocarbon radicals containing from 1 to 6 carbon atoms. The term "halo" is used to embrace chlorine, bromine, iodine and fluorine. The expression "pharmaceutically acceptable salt" is intended to embrace acid addition salts, where applicable or alkali metal or amine salts of the free carboxylic acid formed where R is hydrogen. Examples of acid addition salts include both organic and inorganic non-toxic salts formed with acids such as hydrochloric, hydrobromic, sulfuric, phosphoric, methane sulfonic, nitric, p-toluene sulfonic, acetic, citric, maleic, succinic acid and the like. The alkali metal or amine salts of the free oxamic acid include sodium, potassium, lower alkylamine (e.g. methylamine, ethylamine, propylamine, etc.) di(lower)alkylamine (e.g. dimethylamine, diethylamine, dipropylamine, etc.), di(hydroxyethyl)amine, N,N¹-dibenzyl ethylene diamine, and the like.

The compounds disclosed in this application relieve atopic allergic manifestations, when administered parenterally to sensitized rats.

The technique employed to establish the anti-allergic activity of the N-(pyridyl)oxamic acid derivatives is reported in Immunology, vol. 16, pp. 749,760 (1969) and involves four male Charles River rats (200–250 grams body weight) per group to provide a control, a host for administration of a standard anti-allergic compound (disodium cromoglycate) and animals for the test compound. The rats were injected intracutaneously on their shaved backs with sera from rats immunized with egg albumin and pertussis vaccine. Twenty-four hours after the initial injections, the test compound is administered intraperitoneally or orally at a dosage level of 200 milligrams per kilogram host body weight or less. Five minutes later one milliliter of a 0.5 percent solution of Evans blue dye and 8 milligrams of egg albumin is injected intravenously. After forty minutes, the animal is sacrificed and the bleb size on its back is measured. The mean bleb size for the animals administered the test compound is calculated and the percent inhibition is determined by comparison with the control animal.

Although the mechanism by which the compounds of this invention function is not absolutely known, applicants believe they function in a manner similar to INTAL ®, to block reaction(s) in the mast cell which lead to the production and release of mediators.

The compounds of this invention permit the occurrence of a non-productive antigen-antibody interaction. They effectively block the IgE type reaction and have little or no effect on the other immunoglobulins such as IgG, IgM, IgA and IgD.

In other words, the compounds of this invention block the release of mediators commonly resulting from the antigenantibody reaction as exemplified in a passive cutaneous anaphylaxis test (PCA) using rat homocytotropic antibody - a known correlate of human reaginic antibody.

By analogy to disodium cromoglycate and its activity correlation between standard test animals, domestic animals and man, the compounds of this invention have been established as anti-allergic agents suitable for the same uses at analogous doses and through the same route of administration as INTAL ®.

Thus, there is provided herewith a method for suppressing allergic manifestations of atopic immediate sensitivity in warmblooded, human and non-human animals, the latter including domesticated animals such as the mouse, rat, hamster, gerbil, dog, cat, sheep, goat, horse, cow, and the like, by administering an effective amount of one or more of the compounds disclosed in this application by oral, topical, parenteral, rectal, vaginal or inhalation routes. The compounds of this invention may be administered in conjunction with known compounds effecting anti-histaminic, anti-hypertensive, analgesic, central nervous system depressant, immunosuppressive, anti-serotonin, antiBradykinin or endocrinological responses. In addition, those conventional adjuvants known to the art may be combined with the anti-allergics of this invention to provide compositions and solutions for administrative purposes, although it is considered desireable and feasible to employ the anti-allergics as neat or pure compounds without additives other than for purposes of providing suitable pharmaceutical solution or liquid or vapor suspensions, the latter for use as inhalants.

The oral dose range lies from below 0.01 milligram per kilogram to about 100 milligrams per kilogram host body weight. As an inhalant the dose is from that of INTAL ®, (about 20 milligrams) to 1/20th that quantity administered as needed prior to attack. Thus the dosage contemplated for human use based upon the potency of the compounds administered lies from about 0.5 milligrams to 1 gram, preferably 5 milligrams to about 750 milligrams in unit dosage form to be administered when necessary and to the degree of the desired response, in single or plural doses under the guidance of a physician. Each of the specifically named compounds in the following preparatory examples are active at substantially the same level as the compound presented in Example 1, which effectively inhibited bleb formation by one hundred percent upon intraperitoneal administration of 200 milligrams per kilogram host body weight.

The compounds of this invention are prepared by reaction of an appropriately substituted cyano pyridylamine with a lower alkyl oxalyl chloride ester followed by conversion to the free acid or a pharmaceutically acceptable non-toxic salt; illustrated in Example 14, as desired. The pyridyl amine reactants are either known compounds or are readily preparable by techniques well known in the art.

(3-Cyano-2-pyridyl)oxamic acid ethyl ester

To a solution of 5.95 g. (0.05 mole) of 2-aminonicotinonitrile (E. C. Taylor & A. J. Crovetti, J. Org. Chem. 19, 1633(1954) is 150 ml. of methylenechloride and 7.9 g (0.1 mole) of pyridine is slowly added 6.8 g. (0.05 mole) of ethyloxalyl chloride. After the addition the reaction is stirred for one hour, evaporated to dryness and 5 ml. of water is added. The mixture is filtered and the crude product is recrystallized from methylene chloride-diethyl ether to yield 2.9 g. of pure product, m.p. 95°–97° C.

Elemental Analysis for $C_{10}H_9N_3O_3$; Calc'd: C, 54,79; H, 4.14; N, 19.17 Found: C, 54,59; H, 4.05; N, 18.89

EXAMPLE 2

(3-Cyano-5-methyl-2-pyridyl)oxamic acid ethyl ester

Following the procedure detailed in Example 1, 2-amino-5-methyl-3-pyridine carbonitrile (0.05 mol.) is reacted with ethyloxalyl chloride (0.05mol.) to yield the title compound.

EXAMPLE 3

(2-Cyano-5-bromo or -chloro-3-pyridyl)oxamic acid ethyl ester

Repetition of the procedure of Example 1, with (3-amino-5-bromo-2-cyano)pyridine rather than 2-amino-3-pyridine carbonitrile affords the title compound. The corresponding (5-chloro-2-cyano-3-pyridyl)oxamic acid ethyl ester is produced employing 3-amino-5-chloro-2-pyridine carbonitrile as the initial reactant.

EXAMPLE 4

(3-cyano-6-methyl-2-pyridyl)oxamic acid ethyl ester

Repetition of the process of Example 1, employing 2-amino-6-methyl-3-pyridinecarbonitrile in lieu of 2-amino-3-pyridinecarbonitrile yields the title compound.

EXAMPLE 5

(2-chloro-3-cyano-5-pyridyl)oxamic acid ethyl ester

Following the procedure of Example 1 with the exception that 5-amino-2-chloro-3-pyridinecarbonitrile is substituted for 2-amino-3-pyridinecarbonitrile yields the title compound.

EXAMPLE 6

(3-cyano-6-methyl-5-pyridyl)oxamic acid ethyl ester

Following the procedure of Example 1, while substituting 5-amino-6-methyl-3-pyridinecarbonitrile for 2-amino-3-pyridinecarbonitrile yields the title compound.

EXAMPLE 7

(6-chloro-3-cyano-2-pyridyl)oxamic acid ethyl ester

2-Amino-6-chloro-3-pyridinecarbonitrile (0.05 mol) is reacted with ethyloxalyl chloride (0.05 mol) in accordance with the process of Example 1 to obtain the title compound.

EXAMPLE 8

(2-chloro-3-cyano-6-pyridyl)oxamic acid ethyl ester

Repetition of the procedure of Example 1 with 6-amino-2-chloro-3-pyridinecarbonitrile rather than 2-amino-3-pyridinecarbonitrile affords the title compound.

EXAMPLE 9

(6-chloro-4-cyano-2-pyridyl)oxamic acid ethyl ester

Following the procedure of Example 1, 2-amino-6-chloro-4-pyridinecarbonitrile is reacted with ethyloxalyl chloride to afford the title compound.

EXAMPLE 10

(2-cyano-4-pyridyl)oxamic acid ethyl ester

Following the procedure of Example 1 2-amino-6-chloro-4-pyridinecarbonitrile is reacted with ethyloxalyl chloride to yield the title compound.

EXAMPLE 11

(3-cyano-4-methoxy-5-pyridyl)oxamic acid ethyl ester

Following the procedure of Example 1, 5-amino-4-methoxy-3-pyridinecarbonitrile is reacted with ethyloxyalyl chloride to produce the title compound.

EXAMPLE 12

(3-cyano-2-methoxy-5-pyridyl)oxamic acid ethyl ester

Following the procudure of Example 1, 2-methoxy-5-amino-3-pyridinecarbonitrile is reacted with ethyloxalyl chloride to produce the title compound.

EXAMPLE 13

(3-cyano-4-trifluoromethyl-5-pyridyl)oxamic acid ethyl ester

The title compound is produced by the method of Example 1 with the exception that 5-amino-4-trifluoromethyl-3-pyridinecarbonitrile is employed rather than 2-amino-3-pyridinecarbonitrile.

EXAMPLE 14

(3-Cyano-2-pyridyl)oxamic acid (3-Cyano-2-pyridyl)oxamic acid ethyl ester (0.005 mole) is stirred in 50 ml. water and 5.0 ml. of N NaOH is slowly added. After one half hour the solution is filtered and the filtrate is acidified to pH 2 with N HCl, giving the title compound.

What is claimed is:

1. A process for preventing the release of pharmacological mediators from an immediate hypersensitivity reaction between reaginic type antibodies and an antigen, thereby preventing the symptoms manifest in bronchial asthma, seasonal pollinosis, allergic rhinitis, urticaria, allergic conjunctivitis, food allergy and anaphylactoid reactions of a sensitized animal, which comprises prophylactically administering to said animal an effective amount of a compound of the formula:

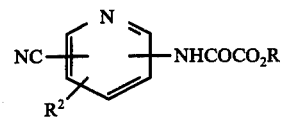

in which R is —H or lower alkyl;
R² is —H, lower alkoxy, lower halo or polyhalo(-lower) alkyl;
or a pharmaceutically acceptable salt thereof.

2. The process of claim 1 in which said compound or salt is administered orally.

3. A compound of the formula:

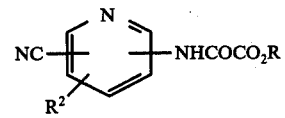

in which R is —H or lower alkyl;
R² is —H, lower alkoxy, lower alkyl, halo or polyhalo (lower)alkyl;
or a pharmaceutically acceptable salt thereof.

4. The compound of claim 3 which is (3-cyano-2-pyridyl)oxamic acid, a lower alkyl ester or a pharmaceutically acceptable salt thereof.

5. The compound of claim 3 which is (3-cyano-5-methyl-2-pyridyl)oxamic acid, a lower alkyl ester or a pharmaceutically acceptable salt thereof.

6. The compound of claim 3 which is (2-Cyano-5-bromo-3-pyridyl)oxamic acid, a lower alkyl ester or a pharmaceutically acceptable salt thereof.

7. The compound of claim 3 which is (3-Cyano-6-methyl-2-pyridyl)oxamic acid, a lower alkyl ester or a pharmaceutically acceptable salt thereof.

8. The compound of claim 3 which is (2-chloro-3-cyano-5-prydiyl)oxamic acid, a lower alkyl ester or a pharmaceutically acceptable salt thereof.

9. The compound of claim 3 which is (3-Cyano-6-methyl-5-pyridyl)oxamic acid, a lower alkyl ester or a pharmaceutically acceptable salt thereof.

10. The compound of claim 3 which is (6-chloro-3-cyano-2-pyridyl)oxamic acid, a lower alkyl ester or a pharmaceutically acceptable salt thereof.

11. The compound of claim 3 which is (2-chloro-3-cyano-6-pyridyl)oxamic acid, a lower alkyl ester or a pharmaceutically acceptable salt thereof.

12. The compound of claim 3 which is (6-chloro-4-cyano-2-pyridyl)oxamic acid, a lower alkyl ester or a pharmaceutically acceptable salt thereof.

13. The compound of claim 3 which is (2-cyano-4-pyridyl)oxamic acid, a lower alkyl ester or a pharmaceutically acceptable salt thereof.

14. The compound of claim 3 which is (3-cyano-4-methoxy-5-pyridyl)oxamic acid, a lower alkyl ester or a pharmaceutically acceptable salt thereof.

15. The compound of claim 3 which is (3-cyano-2-methoxy-5-pyridyl)oxamic acid, a lower alkyl ester or a pharmaceutically acceptable salt thereof.

16. The compound of claim 3 which is (3-cyano-4-trifluoromethyl-5-pyridyl)oxamic acid, a lower alkyl ester or a pharmaceutically acceptable salt thereof.

17. The compound of claim 3 which is (2-cyano-5-chloro-3-pyridyl)oxamic acid, a lower alkyl ester or a pharmaceutically acceptable salt thereof.

* * * * *